United States Patent
Mahanpour et al.

[19]

[11] Patent Number: 6,127,194
[45] Date of Patent: Oct. 3, 2000

[54] PACKAGE REMOVAL FOR FBGA DEVICES

[75] Inventors: Mehrdad Mahanpour, Union City; Mohammad Massoodi, Campbell, both of Calif.

[73] Assignee: Advanced Micro Devices, Inc., Sunnyvale, Calif.

[21] Appl. No.: 09/208,826

[22] Filed: Dec. 9, 1998

[51] Int. Cl.[7] ...................................................... G01R 31/26
[52] U.S. Cl. ..................................... 438/14; 438/4; 438/8; 438/12; 438/71; 438/691; 438/689; 257/48
[58] Field of Search ..................................... 257/784, 787, 257/781, 782, 737, 779, 687, 688, 693, 48; 438/8, 15, 14, 71, 689, 690, 691, FOR 101, FOR 126, FOR 142, 692, 694, 4, 12

[56] References Cited

U.S. PATENT DOCUMENTS

| | | | |
|---|---|---|---|
| 5,650,593 | 7/1997 | McMillan et al. | 257/779 |
| 5,861,662 | 1/1999 | Candelore | 257/679 |

*Primary Examiner*—Tom Thomas
*Assistant Examiner*—Luan Thai
*Attorney, Agent, or Firm*—Sawyer Law Group

[57] ABSTRACT

Aspects for removing device packaging from an FBGA (fine pitch ball grid array) package are described. In an exemplary method aspect, the method includes recessing a predetermined area of the FBGA package, and exposing an integrated circuit die covered by the FBGA package. Device analysis is then performed on the exposed die. The step of recessing further includes milling the predetermined area, while the step of exposing includes chemically etching the FBGA package.

9 Claims, 2 Drawing Sheets

6,127,194

PACKAGE REMOVAL FOR FBGA DEVICES

FIELD OF THE INVENTION

The present invention relates to all plastic packaged devices, and more particularly to package removal of fine-pitch ball grid array (FBGA) devices.

BACKGROUND OF THE INVENTION

With the advancements in semiconductor device technology, several different types of package arrangements for integrated circuit devices have emerged. One type of arrangement to have emerged is the fine ball grid array (FBGA) device. An example of a typical FBGA device is illustrated in FIG. 1 by a partial cross-sectional diagram.

As shown in FIG. 1, an FBGA device 8 typically includes an integrated circuit die 10 encapsulated in packaging material 12, e.g., an epoxy compound. Electrical connections for the die 10 are provided by bond wires 14, such as gold wires, coupling input/output pads on the die 10 to bond pads 16 of a die paddle 18, e.g., an elastomer material. The bond pads 16 couple the die 10 to solder ball connectors 20 via electrical connector tracings 22, e.g., copper tracings, in a tape material 24, e.g., a polyimide tape. The solder ball connectors 20 may then be used to capably attach the device 8 to a circuit board (not shown).

In order to perform device analysis, normally the package 12 must be removed to reveal the surface of die 10 and bond wires 14. Chemical etching is commonly performed to remove the package 12. Unfortunately, a difficulty exists in precisely controlling the chemical etching, since the etching of the package 12 typically results in overetching of the package 12. The overetching often damages the bond wires 14, which destroys the ability to electrically test the circuit. Further, without sufficient package material on an edge portion of the device, the device cannot be adequately secured in a testing socket and device analysis is unable to be performed.

Accordingly, a need exists for a package removal procedure for an FBGA device to allow successful device analysis. The present invention addresses such a need.

SUMMARY OF THE INVENTION

The present invention provides aspects for removing device packaging from an FBGA (fine ball grid array) package. In an exemplary method aspect, the method includes recessing a predetermined area of the FBGA package, and exposing an integrated circuit die covered by the FBGA package. Device analysis is then performed on the exposed die. The step of recessing further includes milling the predetermined area, while the step of exposing includes chemically etching the FBGA package.

Through the present invention, overetching of package material and bond wires is successfully avoided. Further, an edge portion is more readily maintained on the package to better facilitate securing the package in a test socket during device analysis. These and other advantages of the aspects of the present invention will be more fully understood in conjunction with the following detailed description and accompanying drawings.

DETAILED DESCRIPTION

The present invention relates to package removal for FBGA devices. The following description is presented to enable one of ordinary skill in the art to make and use the invention and is provided in the context of a patent application and its requirements. Various modifications to the preferred embodiment and the generic principles and features described herein will be readily apparent to those skilled in the art.

Figure 1:
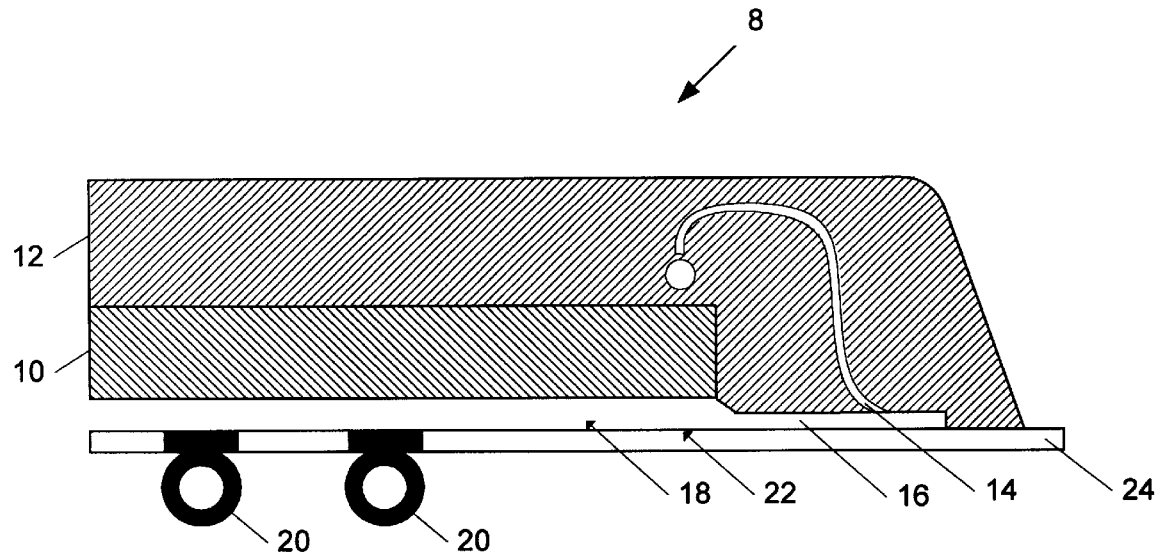
FIG. 1 illustrates a partial cross-section diagram of a typical FBGA device.
Figure 2:
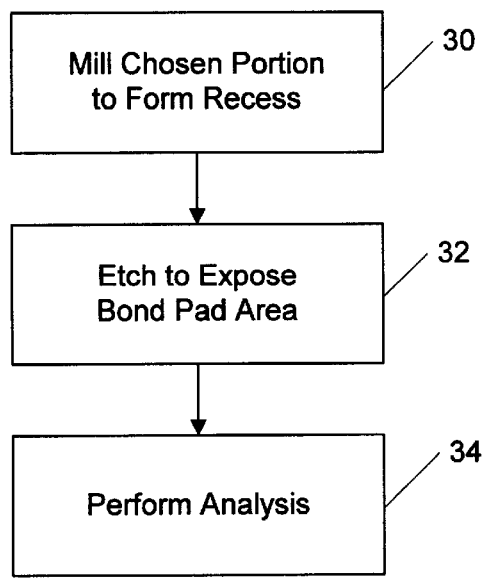
FIG. 2 illustrates a block flow diagram of a process for FBGA package removal in accordance with the present invention.
Figure 3:
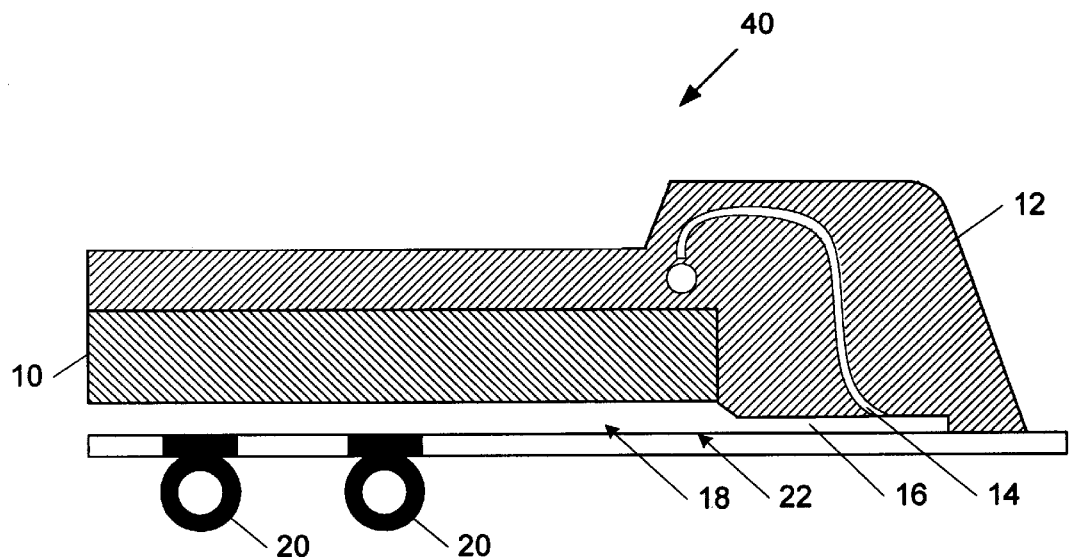
FIGS. 3 and 4 illustrate partial cross-sectional diagrams of an FBGA device during the processing of FIG. 2.
Figure 4:
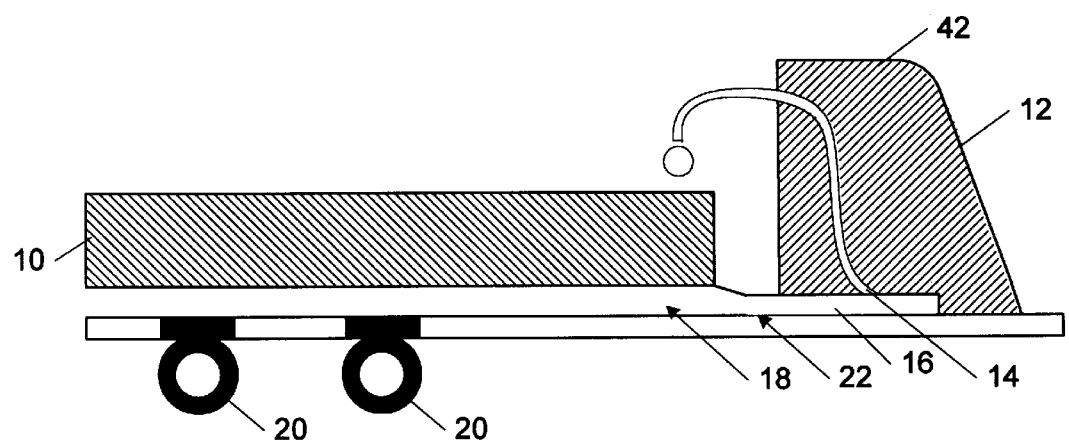

FIG. 2 illustrates a block flow diagram of a process for package removal for an FBGA device in accordance with the present invention. FIGS. 3 and 4 illustrates partial cross-sectional diagrams of an FBGA device during the process of FIG. 2. Referring to FIG. 2, the process for package removal initiates with milling a predetermined amount of a chosen portion of a device package to form a recessed area (step 30). In a preferred embodiment, the package portion substantially over a die surface is the chosen portion of the package being milled. A computerized programmable milling device is suitable for performing the milling to remove the predetermined amount of the package. The predetermined amount removed is dependent upon the package thickness and device area, as is well appreciated by those skilled in the art. As an example, however, for the typical device represented in FIG. 1, approximately half of the package covering the surface of the die is removed by milling.

FIG. 3 illustrates a partial cross-sectional diagram of an FBGA device following step 30 of FIG. 2. Corresponding elements are labeled similarly to FIG. 1. As shown in FIG. 3, the milling step results in the recessed area 40 being formed in package 12 substantially over the area of the surface of die 10.

Referring again to FIG. 2, once the recessed area 40 has been formed through milling, the process continues with chemical etching of the package 12 to reveal the bond pad area (step 32). The resulting device is then analyzed as desired (step 34) using standard device analysis techniques for an FBGA device. The chemical etching of the package 12 preferably occurs using conventional etching techniques. However, the reduced thickness of the package 12 through the formation of the recessed area 40 in the package 12 results in a faster etching of that portion of the package 12.

FIG. 4 illustrates a partial cross-section of the FBGA device following step 32. As shown, a sufficient edge portion 42 of the package 12 remains following the etching to allow the device to be held in a socket during the analysis step 34. In a preferred embodiment, about 0.8 mm (millimeters) of package material is maintained for the edge portion 42 in order to be held in a testing socket. Further, the faster etching of the package 12 in the recessed area 40 effectively results in the desired exposure of the bond wires 14, while substantially eliminating potential overetching of the bond wires 14. Thus, successful electrical testing of the device during the analysis readily occurs.

Although the present invention has been described in accordance with the embodiments shown, one of ordinary skill in the art will recognize that there could be variations to the embodiment and those variations would be within the spirit and scope of the present invention. Accordingly, many modifications may be made by one of ordinary skill without departing from the spirit and scope of the present invention, the scope of which is defined by the following claims.

What is claimed is:

1. A method for exposing a die surface of a fine ball grid array (FBGA) device, the method comprising the steps of:

milling a chosen portion of a package covering the die surface a predetermined amount; and chemically etching the package to expose the die surface, wherein over etching of a bond pad is avoided, including stopping etching before an edge portion of said package of the FBGA device is etched and utilizing the edge portion of said package to secure the FBGA device in a socket for device testing.

2. The method of claim 1 further comprising performing device analysis of the FBGA device with the exposed die surface.

3. The method of claim 1 wherein the edge portion comprises a package edge of about 0.8 mm.

4. The method of claim 1 wherein the step of milling a predetermined amount further forms a recessed area over the die surface.

5. A method for removing device packaging from a FBGA (fine ball grid array) package, the method comprising:

recessing a predetermined area of the FBGA package;

exposing an integrated circuit die covered by the FBGA package by chemically etching the FBGA package to maintain a predetermined edg portion of the FBGA packae; and performing device analysis on the exposed die while securing the FBGA device at the predetermined edge portion in a socket.

6. The method of claim 5 wherein the step of recessing further comprises milling the predetermined area.

7. The method of claim 5 wherein the predetermined area comprises a package area covering a surface of the integrated circuit die.

8. The method of claim 5 wherein the predetermined edge portion comprises a edge of about 0.8 mm.

9. The method of claim 5 wherein performing device analysis further comprises performing electrical testing.

* * * * *